(12) United States Patent
Westerly et al.

(10) Patent No.: US 7,977,648 B2
(45) Date of Patent: Jul. 12, 2011

(54) SCANNING APERTURE ION BEAM MODULATOR

(75) Inventors: David C. Westerly, Madison, WI (US); Thomas R. Mackie, Verona, WI (US); Ryan T. Flynn, Iowa City, IA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 379 days.

(21) Appl. No.: 12/305,554

(22) PCT Filed: Feb. 27, 2008

(86) PCT No.: PCT/US2008/055090
§ 371 (c)(1),
(2), (4) Date: Dec. 18, 2008

(87) PCT Pub. No.: WO2008/106492
PCT Pub. Date: Sep. 4, 2008

(65) Prior Publication Data
US 2009/0289192 A1 Nov. 26, 2009

Related U.S. Application Data

(60) Provisional application No. 60/891,859, filed on Feb. 27, 2007.

(51) Int. Cl.
*H01J 3/14* (2006.01)
*A61N 5/00* (2006.01)
(52) U.S. Cl. ............ 250/396 R; 250/492.22; 250/492.3
(58) Field of Classification Search ................ 250/96 R, 250/397, 398, 492.3, 492.1, 492.21, 492.22, 250/492.23
See application file for complete search history.

(56) References Cited

U.S. PATENT DOCUMENTS

| | | | |
|---|---|---|---|
| 4,276,477 A | 6/1981 | Enge | |
| 5,317,616 A | 5/1994 | Swerdloff et al. | |
| 5,394,452 A | 2/1995 | Swerdloff et al. | |
| 5,442,675 A | 8/1995 | Swerdloff et al. | |
| 5,528,650 A | 6/1996 | Swerdloff et al. | |
| 5,548,627 A | 8/1996 | Swerdloff et al. | |
| 5,625,663 A | 4/1997 | Swerdloff et al. | |
| 5,661,773 A | 8/1997 | Swerdloff et al. | |
| 5,668,371 A | 9/1997 | Deasy et al. | |
| 5,673,300 A | 9/1997 | Reckwerdt et al. | |
| 5,724,400 A | 3/1998 | Swerdloff et al. | |
| 5,802,136 A | 9/1998 | Carol | |
| 6,345,114 B1 | 2/2002 | Mackie et al. | |

(Continued)

FOREIGN PATENT DOCUMENTS

DE 19907098 A1 8/2000

(Continued)

OTHER PUBLICATIONS

International Search Report, PCT Application No. PCT/US2008/055104, dated Jul. 17, 2008, ISA/EPO, 2280 HV Rijswijk, NL.

(Continued)

*Primary Examiner* — Bernard E Souw
(74) *Attorney, Agent, or Firm* — Boyle Fredrickson, S.C.

(57) ABSTRACT

A modulator for ions such as protons employs multiple shutter pairs to create independently movable apertures effecting a multiple pencil beam treatment of the patient thereby increasing treatment speed by eliminating the need for a custom compensator.

25 Claims, 4 Drawing Sheets

U.S. PATENT DOCUMENTS

| | | | |
|---|---|---|---|
| 6,385,286 B1 | 5/2002 | Fitchard et al. | |
| 6,438,202 B1 | 8/2002 | Olivera et al. | |
| 6,560,311 B1 | 5/2003 | Shepherd et al. | |
| 6,618,467 B1 | 9/2003 | Ruchala | |
| 6,636,622 B2 | 10/2003 | Mackie et al. | |
| 6,661,870 B2 | 12/2003 | Kapotoes et al. | |
| 6,731,970 B2 | 5/2004 | Schlossbauer et al. | |
| 6,915,005 B1 | 7/2005 | Ruchala et al. | |
| 7,046,831 B2 | 5/2006 | Ruchala et al. | |
| 7,186,986 B2 | 3/2007 | Hinderer et al. | |
| 7,207,715 B2 | 4/2007 | Yue | |
| 7,302,038 B2 | 11/2007 | Mackie | |
| 7,714,309 B2 * | 5/2010 | Mackie et al. | 250/492.3 |
| 2002/0136439 A1 | 9/2002 | Ruchala et al. | |
| 2003/0160189 A1 | 8/2003 | Matsuda | |
| 2003/0198319 A1 | 10/2003 | Toth et al. | |
| 2005/0123092 A1 | 6/2005 | Mistretta et al. | |
| 2005/0197564 A1 | 9/2005 | Dempsy | |
| 2006/0226372 A1 | 10/2006 | Yanagisawa | |
| 2006/0285639 A1 | 12/2006 | Olivera et al. | |
| 2007/0029510 A1 | 2/2007 | Hermann | |
| 2007/0036267 A1 | 2/2007 | Becker et al. | |
| 2007/0041494 A1 | 2/2007 | Ruchala et al. | |
| 2007/0041495 A1 | 2/2007 | Olivera et al. | |
| 2007/0041496 A1 | 2/2007 | Olivera et al. | |
| 2007/0041497 A1 | 2/2007 | Schnarr et al. | |
| 2007/0041498 A1 | 2/2007 | Olivera et al. | |
| 2007/0041499 A1 | 2/2007 | Lu et al. | |
| 2007/0041500 A1 | 2/2007 | Olivera et al. | |
| 2007/0043286 A1 | 2/2007 | Lu et al. | |
| 2007/0076846 A1 | 4/2007 | Ruchala et al. | |
| 2007/0104316 A1 | 5/2007 | Ruchala et al. | |
| 2007/0195922 A1 | 8/2007 | Mackie et al. | |
| 2007/0195929 A1 | 8/2007 | Ruchala et al. | |
| 2007/0195930 A1 | 8/2007 | Kapotoes et al. | |
| 2007/0242801 A1 | 10/2007 | Mackie et al. | |
| 2008/0260098 A1 * | 10/2008 | Al-Sadah et al. | 378/65 |
| 2009/0200481 A1 * | 8/2009 | Mackie et al. | 250/396 ML |

FOREIGN PATENT DOCUMENTS

| | | | |
|---|---|---|---|
| EP | 0986070 A | 3/2000 | |
| EP | 1045399 A | 10/2000 | |
| JP | 2000 214298 A | 8/2000 | |
| WO | WO2002/07817 A | 1/2002 | |
| WO | WO2002/41948 A | 5/2002 | |
| WO | WO2005/004168 A | 1/2005 | |
| WO | WO2007/021226 A | 2/2007 | |

OTHER PUBLICATIONS

International Search Report, PCT Application No. PCT/US2008/055070, dated Jul. 17, 2008, ISA/EPO, 2280 HV Rijswijk, NL.

International Search Report, PCT Application No. PCT/US2008/055069, dated Jul. 17, 2008, ISA/EPO, 2280 HV Rijswijk, NL.

International Search Report, PCT Application No. PCT/US2008/055161, dated Jul. 17, 2008, ISA/EPO, 2280 HV Rijswijk, NL.

International Search Report, PCT Application No. PCT/US2008/055083, dated Jul. 17, 2008, ISA/EPO, 2280 HV Rijswijk, NL.

International Search Report, PCT Application No. PCT/US2008/055096 dated Jul. 17, 2008, ISA/EPO, 2280 HV Rijswijk, NL.

International Search Report, PCT Application No. PCT/US2008/055090 dated Jul. 17, 2008, ISA/EPO, 2280 HV Rijswijk, NL.

International Search Report, PCT Application No. PCT/US2008/055147, dated Jul. 25, 2008, ISA/EPO, 2280 HV Rijswijk, NL.

Baumert, BG, et al., Dose conformation of intensity-modulated stereotactic photon beams, proton beams, and intensity-modulated proton beams for intracranial lesions, Int. J. Radiat. Oncol. Biol. Phys., 2005, 60:1314-1324, Elsevier, Amsterdam, Netherlands.

Deasy, JO, et al., Distal edge tracking: a proposed delivery method for conformal proton therapy using intensity modulation, 1997, pp. 406-409, Proceedings of the XIIth International Congress on Computers in Radiotherapy May 27-30, 1997, Salt Lake City, IEEE Publishing, Los Alamitos, California, USA.

Deasy, JO, A proton dose calculation algorithm for conformal therapy simulations based on Moliere theory of lateral deflections, Med. Phys., Apr. 1998, 25:476-483, American Association of Physical Medicine, New York, New York.

Lomax, AJ, Intensity modulation methods for proton radiotherapy, Phys. Med. Biol., 1999 44:185-205, IOP Publishing Ltd., Bristol, UK.

Lomax, AJ, et al. Intensity modulated proton therapy: A clinical example, Mar. 2001, Med. Phys. 28:317-324, , American Association of Physical Medicine, New York, New York.

Lomax, AJ, Compensated and intensity-modulated proton therapy, in Palta J, and Mackie TR (eds), Intensity Modulated Radiation Therapy: The State of the Art, Nov. 2004, pp. 787-828, Medical Physics Publishing Madison, WI.

Lomax, AJ, et al., Treatment planning and verification of proton therapy using spot scanning: initial experiences. 2004a, Med. Phys. 31:3150-3157, American Association of Physical Medicine, New York, New York.

Lomax, AJ, et al., The clinical potential of intensity modulated proton therapy, 2004b, Z. Med. Phys. 14:147-152, Elsevier, Amsterdam, Netherlands.

Kanai, T, et al., Spot scanning system for proton radiotherapy, Jul./Aug. 1980, Med. Phys 7:365-369, American Association of Physical Medicine, New York, New York.

Moyers MF, (Proton therapy, Van Dyk (ed), The Modern Technology of Radiation Oncology, 1999, pp. 823-869, Medical Physics Publishing, Madison, WI.

Nill, S, et al., Inverse planning of intensity modulated proton therapy, 2004, Z Med. Phys. 14:35-40, Elsevier, Amsterdam, Netherlands.

Oelfke U, et al., Intensity modulated radiotherapy with charged particle beams: Studies of inverse treatment planning for rotation therapy. Jun. 2000, Med. Phys, 27:1246-1257, American Association of Physical Medicine, New York, New York.

Paganetti H, Proton Therapy: A Workshop Handout. 2005, Private Communication, Massachusetts General Hospital, Boston, MA.

Sampayan S, et al. Development of a compact radiography accelerator using dielectric wall accelerator technology, Jun. 6, 2005, Proceed. Int. Pulsed Power Conf. Monterey, CA, Lawrence Livermore Laboratory, Livermore, CA.

Wilson RW., Radiological use of fast protons. Nov. 1946, Radiology 47:487-491, Radiological Society of North America, Easton, Pennsylvania.

Yu C., Intensity modulated arc therapy with dynamic multileaf collimation: an alternative to tomotherapy, 1995, Phys. Med. Biol. 40:1435-1449, IOP Publishing Ltd., Bristol, UK.

Anferov V., Combined X-Y scanning magnet for conformal proton radiation therapy, Med. Phys., Mar. 2005, 32:815-818, American Association of Physical Medicine, New York, New York.

Goitlein, M., Beam scanning for heavy charged particle radiotherapy, Nov./Dec. 1983, Med. Phys. 10 (6) pp. 831-840, American Association of Physical Medicine, New York, New York.

* cited by examiner

SCANNING APERTURE ION BEAM MODULATOR

CROSS-REFERENCE TO RELATED APPLICATIONS

This application claims the benefit of U.S. Provisional Application 60/891,859, filed Feb. 27, 2007, and PCT Application PCT/US2008/055090, filed Feb. 27, 2008, the disclosures of which are incorporated herein by reference.

STATEMENT REGARDING FEDERALLY SPONSORED RESEARCH OR DEVELOPMENT

This invention was made with United States government support awarded by the following agency: NIH CA088960. The United States has certain rights in this invention.

BACKGROUND OF THE INVENTION

The present invention relates to radiation therapy systems using ions, such as protons, for the treatment of cancer and the like and, in particular, to a system providing improved modulation of an ion beam.

External beam radiation therapy may treat a tumor within the patient by directing high-energy radiation in one or more beams toward the tumor. Recent advanced external beam radiation systems, for example, as manufactured by Tomotherapy, Inc., treat a tumor with multiple x-ray fan beams directed at the patient over an angular range of 360°. Each of the beams is comprised of individually modulated beamlets whose intensities can be controlled so that the combined effect of the beamlets, over the range of angles, allows an arbitrarily complex treatment area to be irradiated.

X-rays deposit energy in tissue along the entire path between the x-ray source and the exit point in the patient. While judicious selection of the angles and intensities of the x-ray beamlets can minimize radiation applied to healthy tissue outside of the tumor, inevitability of irradiating healthy tissue along the path to the tumor has suggested the use of ions such as protons as a substitute for x-ray radiation. Unlike x-rays, protons may be controlled to stop within the tissue, reducing or eliminating exit dose through healthy tissue on the far side of the tumor. Further, the dose deposited by a proton beam is not uniform along the entrance path of the beam, but rises substantially to a "Bragg peak" near a point where the proton beam stops within the tissue. The placement of Bragg peaks inside the tumor allows for improved sparing of normal tissue for proton treatments relative to x-ray treatments.

Unlike photon (e.g. x-ray) radiation therapy, radiation therapy with protons or other ions allows separate control of intensity (i.e., the number of protons per second within an area) and energy (i.e., the speed of the protons). Control of the intensity and time of exposure determines the total dose delivered by the protons to tissue, while control of the energy of the protons, by virtue of the Bragg peak described above, controls the depth of the exposure within the tissue.

Current proton therapy systems adopt one of two general approaches. In the first approach, the proton beam is expanded to subtend the entire tumor and the energy of the protons, and hence their stopping point in the tissue, is spread in range, to roughly match the tumor depth. Precise shaping of the exposure volume is provided by a specially constructed range correction compensator which provides additional range shifting to conform the distal edge of the beam to the distal edge of the tumor. This treatment approach essentially treats the entire tumor at once and, thus, is fast and yet less precise and requires the construction of a special compensator.

In a second approach, the proton beam remains narrowly collimated in a "pencil beam" and is steered in angle and adjusted in range to deposit the dose as a small spot within the patient. The spot is moved through the tumor in successive exposures until an arbitrary tumor volume has been irradiated. This approach is potentially very accurate, but because the tumor is treated in successive exposures, is slower than the first approach. Further the small spot sizes create the risk of uneven dose placement or "cold spots" should there be patient movement between exposures.

The complexity of these techniques normally limits the treatment to a single or small number of angles about the patient. This can reduce the level of conformity of the radiation dose to the target tumor because of this strong asymmetry of the Bragg peak of the protons.

BRIEF SUMMARY OF THE INVENTION

The present invention provides the benefit of a scanning pencil beam while greatly increasing treatment speed. This is done by using a beam modulator that takes an area beam (as opposed to a pencil beam) and effectively creates multiple independent pencil beams that may simultaneously treat the patient. The modulator may independently control both intensity and energy of each pencil beam, reducing or eliminating the need for a custom compensator.

Specifically the present invention employs an area beam of ions directed along an axis and having a longitudinal and latitudinal extent in cross-section. The area beam is controllably occluded with a set of longitudinally opposed latitudinally adjacent shutter pairs, each shutter of each pair controllable and extendable to different longitudinal distances. The shutters may thus simultaneously control multiple discrete beams, which are actually portions of the area ion beam, at different adjacent latitudinal positions with controllably independent longitudinal positions. The shutters may control either or both the intensity and energy of the ion beams.

It is thus an object of one embodiment of the invention to increase the treatment speed of the patient by using multiple, independently controllable beams.

Each shutter pair may comprise opposed shutters that can fully block the ion beam from passing through the shutter. The shutter pairs can be moved to control a dwell time of an aperture formed between the shutters to control the intensity of the ion beam at a variety of longitudinal locations.

It is thus one object of one embodiment of the invention to provide a method of operating shutters to independently control the intensity of the separate ion beams.

The shutter pairs may be controlled to move a center of an aperture created between the shutter pairs and to change a longitudinal separation between the shutter pairs.

It is thus an object of one embodiment of the invention to permit control of the longitudinal dimension of each ion beam independently from its longitudinal position. In this way longitudinally adjacent areas of the patient requiring identical or similar intensities may be simultaneously treated further reducing treatment time.

Each shutter may be constructed of multiple blades, each sized to only partially block the ion beam from passing through the blade. The multiple blades may be independently adjusted to control an amount of overlap among the blades and a longitudinal location of the overlap to in turn control the energy of the ion beam at a variety of longitudinal locations.

It is thus an object of one embodiment of the invention to provide a method of simultaneously controlling the energy of the multiple independent ion beams.

The multiple blades of each shutter pair when fully overlapping along an axis of the ion beam may fully block passage of the ion beam, and the multiple blades of each shutter pair may be further controlled to control a dwell time of an aperture formed between the multiple blades to control the intensity of the ion beam at a variety of longitudinal locations.

It is thus an object of one embodiment of the invention to provide a system that may control both the energy and intensity of multiple simultaneous beams.

The area beam may have a non-uniform intensity distribution and the dwell time may be controlled according to the non-uniform intensity distribution and the desired treatment intensity to correct for the non-uniform intensity distribution.

It is thus another object of one embodiment of the invention to permit the generation of an area beam having lower uniformity to reduce the generation of undesired neutrons.

The blades of each shutter pair have equal thicknesses.

It is thus an object of one embodiment of the invention to provide a shutter system that may implement in a piecewise fashion an arbitrary attenuating compensator. The equal thickness shutters allow a complex, energy profile to be developed. The term "equal thickness" is intended to include shutters of different materials and different thickness so as to operate as if they were of equal thicknesses of a single material.

Alternatively the blades of each shutter pair may have different according to a binary sequence.

It is thus an object of one embodiment of the invention to provide the high resolution in energy control with a limited number of blades.

The area beam may be rotated about a patient to provide treatment of the patient at a plurality of angles.

It is thus an object of one embodiment of the invention to provide a system that has suitable speed to permit a large number of angles of patient treatment to be practical.

These particular features and advantages may apply to only some embodiments falling within the claims and thus do not define the scope of the invention.

DETAILED DESCRIPTION OF THE PREFERRED EMBODIMENT

Figure 1:
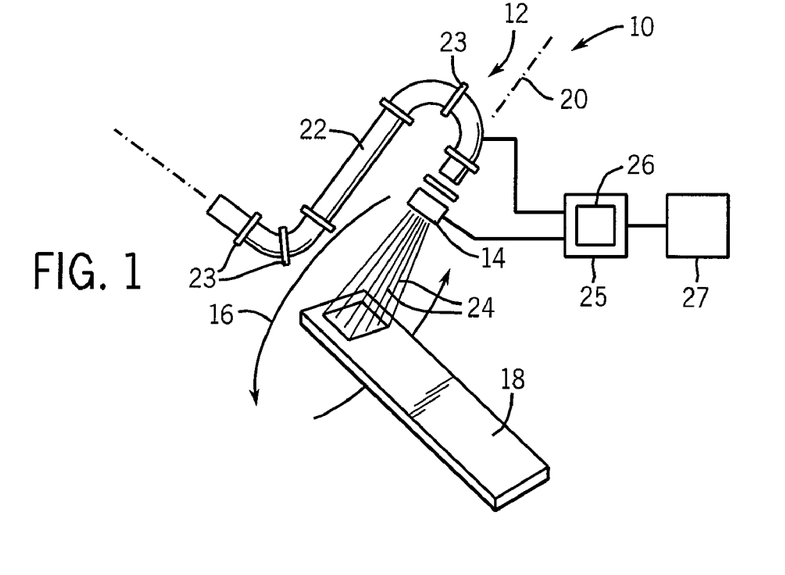
FIG. 1 is a simplified representation of a proton therapy machine suitable for use with the present invention and having a rotating gantry and a modulator directing multiple independent pencil beams of protons toward a patient support at a range of angles.

Referring now to FIG. 1, a proton therapy machine 10 may include a gantry 12 having a modulator 14, both of which may orbit 16 about a patient (not shown) who is supported on a patient support table 18.

The modulator 14 receives a source of protons from a proton source conduit 22 that may conduct protons from a synchrotron, cyclotron or the like and, by means of bending magnets 23, direct them toward the patient support table 18 at all positions within the orbit 16.

The protons from the proton source conduit 22 will generally be narrowly collimated to a pencil beam (not shown) when received by the modulator 14. The modulator 14 spreads the pencil beam into an area beam radiating along an axis 20, and individually modulates independently positionable beamlets 24 (e.g., pencil beams) in energy and intensity. The beamlets 24 are controlled by a control computer 25 communicating with the modulator 14, the control computer 25 executing a stored program 26 to provide control signals to the modulator 14 according to stored treatment sinograms 27 indicating desired intensities and energies of the individual beamlets 24 as a function of the angle of the gantry 12 in orbit 16.

Figure 2:
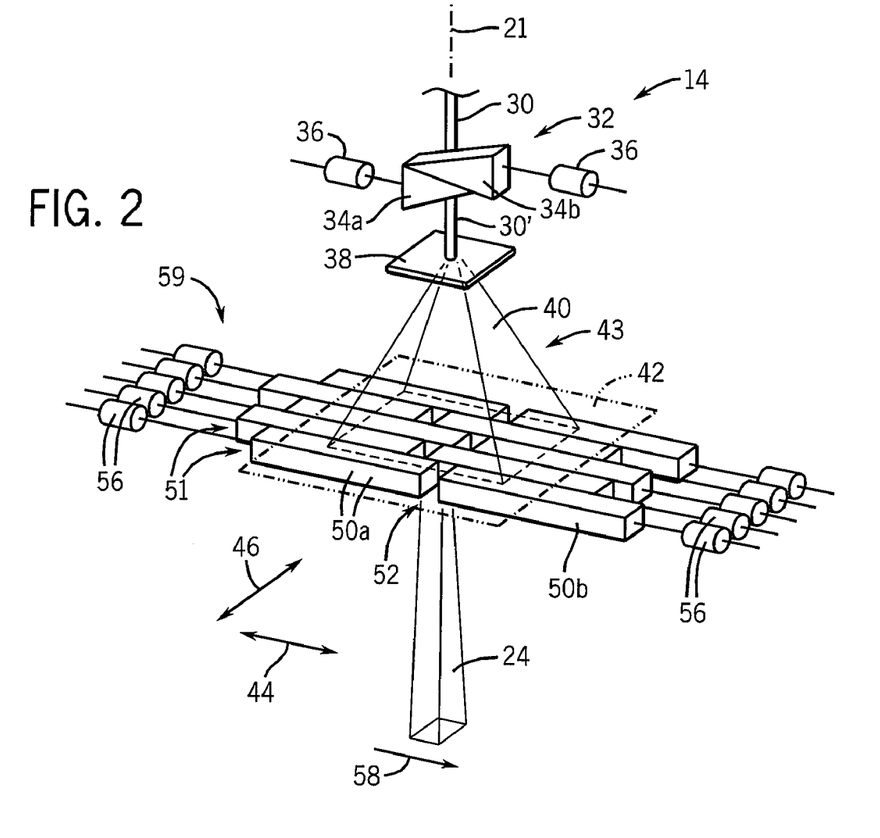
FIG. 2 is an exploded isometric representation of a first embodiment of the modulator using multiple, ion-opaque modulation elements for controlling the intensity of the individual pencil beams.

Referring now to FIG. 2, in a first embodiment, the modulator 14 receives a pencil beam 30 along axis 21 and directs it to an energy modulator 32, in this case, being a pair of opposed wedges 34a and 34b. These two wedges 34a and 34b overlap to present a rectangular cross-section within the beam 30. The amount of overlap, and thus the thickness of the cross-section, is controlled by moving the wedges 34a and 34b to increasing or decreasing overlap by means of electrically controlled actuators 36, the latter receiving signals from computer 25. The thickness of wedge material within the beam 30 controls the energy of the proton in the exiting energy modulated pencil beam 30'. An alternative energy modulator (not shown) is a dielectric wall accelerator which can adjust the acceleration of the ions electrically thus eliminating the neutron production incident to systems that reduce energy of an existing ion beam.

The energy modulated pencil beam 30' may next be received by a scattering foil 38 which spreads the pencil beam 30' into an area beam 40. The area beam 40 radiates along axis 21 spreading in a longitudinal extent 44 and a latitudinal extent 46. Normally the latitudinal extent 46 will be parallel to an axis of the orbit 16, however the opposite orientation with the longitudinal extent 44 parallel with the axis of the orbit 16 may also be used.

The area beam 40 may be masked to a rectangular cross-sectional area 43 by collimator 42 to be received by an area modulator 59 including a set of shutter pairs 51 forming independent modulation elements. The shutter pairs 51 are latitudinally adjacent to each other so that when the shutters are closed (as will be described) they fully fill the cross-sectional area 43.

Each shutter pair 51 includes a left and right shutter 50a and 50b, respectively, the shutters 50a and 50b extending longitudinally and independently movable in the longitudinal direction toward and away to define a controllable aperture 52 therebetween. The aperture 52 thus formed may be controlled in longitudinal width and longitudinal center-point location.

Generally, each shutter 50a and 50b will be opaque to the proton beam, blocking all radiation except that passing through the aperture 52 as beamlet 24. Accordingly, the shutter pairs 51 together convert the area beam 40 into a plurality of independently controllable beamlets 24 corresponding to each aperture 52. In operation the apertures 52, and hence the beamlets 24, will be scanned longitudinally as indicated by direction arrow 58.

The position of each shutter 50a and 50b is controlled by a respective actuator 56 electrically communicating with the computer 25.

Figure 3:
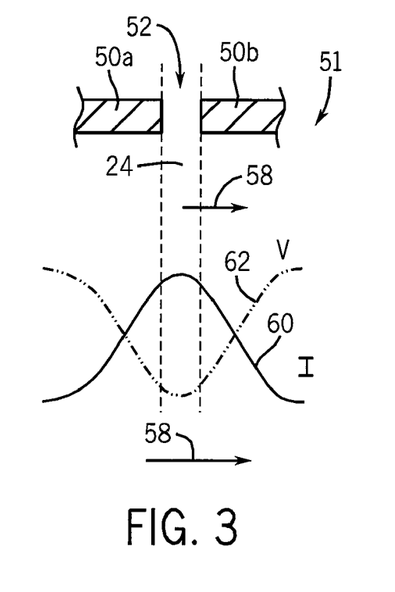
FIG. 3 is a side elevational view of one modulation element showing movement of a shutter pair for intensity modulation.

Referring now also to FIG. 3, by moving the shutters 50a and 50b for each shutter pair 51 along direction arrow 58 and controlling the velocity 62 of longitudinal movement of the aperture 52, the average intensity 60 of radiation directed toward the patient from the beamlet 24 (during the treatment) may be controlled as inversely related to the velocity 62. Thus, when the beamlet 24 dwells for a longer period of time at a given longitudinal position, the total proton flux, and thus dose, increases correspondingly.

It will be understood that multiple beamlets 24 generated by the modulator 14 may have their scanning speed independently controlled to independently control the dose delivered by each of the beamlets 24. This control may be done in parallel so treatment by each beamlet 24 may occur simultaneously.

Figure 4:
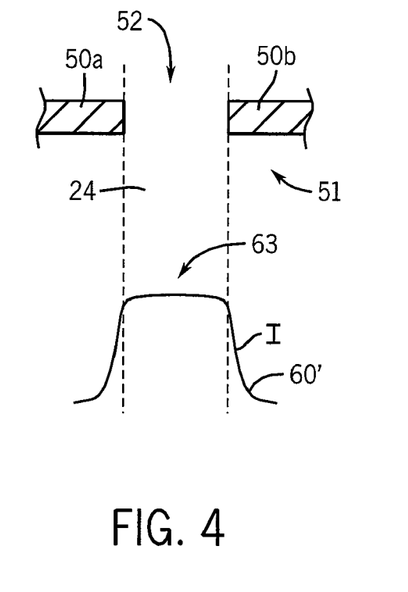
FIG. 4 is a figure similar to that of FIG. 3 showing the movement of the shutter pair for beam width control.

Referring now to FIG. 4, the ability to move the shutters 50a and 50b independently also allows the longitudinal size of the aperture 52 to be changed. This allows widening the aperture when longitudinally adjacent portions of the tumor require identical treatment resulting in a greater efficiency of treatment. For example if an intensity 60' has a plateau portion 63 with essentially constant longitudinal intensity, the beamlet 24 may be widened to equal the width of this plateau portion 63, decreasing treatment time over that which would be required by separate sequential treatments using narrower beamlets 24.

Figure 5:
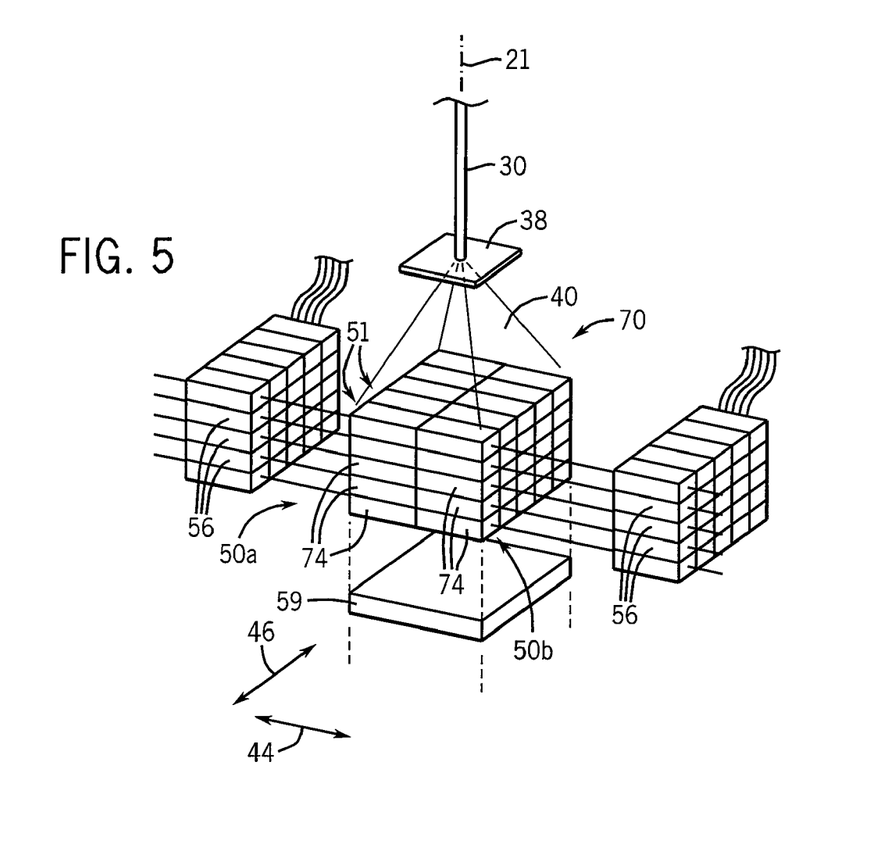
FIG. 5 is a figure similar to that of FIG. 2 showing a second embodiment of the modulator having multiple, energy attenuating modulation elements for controlling the energy of the individual pencil beams and optionally including the modulator of FIG. 2.

Referring now to FIG. 5, in an alternative embodiment, the energy modulator 32 may be eliminated and the pencil beam 30 may be received directly by a scattering foil 38 (or the like) to generate the area beam 40. The area beam 40 may then be received (after collimation to a rectangular area by collimator 42, not shown) by an energy modulator 70.

Like the area modulator 59 shown in FIG. 2, the energy modulator 70 also includes shutter pairs 51 providing corresponding modulation elements. Each shutter pair 51 may again include opposed, longitudinally extending shutters 50a and 50b that may be moved toward and away from each other by actuators 56. In this case, however, each shutter 50a and 50b is comprised of a number of independently movable blades 74 that overlap along the direction of axis 21. The actuators 56 may independently move each of the blades 74 of shutters 50a and 50b.

As before, multiple shutter elements 51 are arranged latitudinally adjacent to fill the cross-sectional area 43 of the collimated area beam 40. As before, each shutter pair 51 may create an aperture independently controlling one latitudinal beamlet 24 (not shown in FIG. 5).

Figures 6, 7, 8:
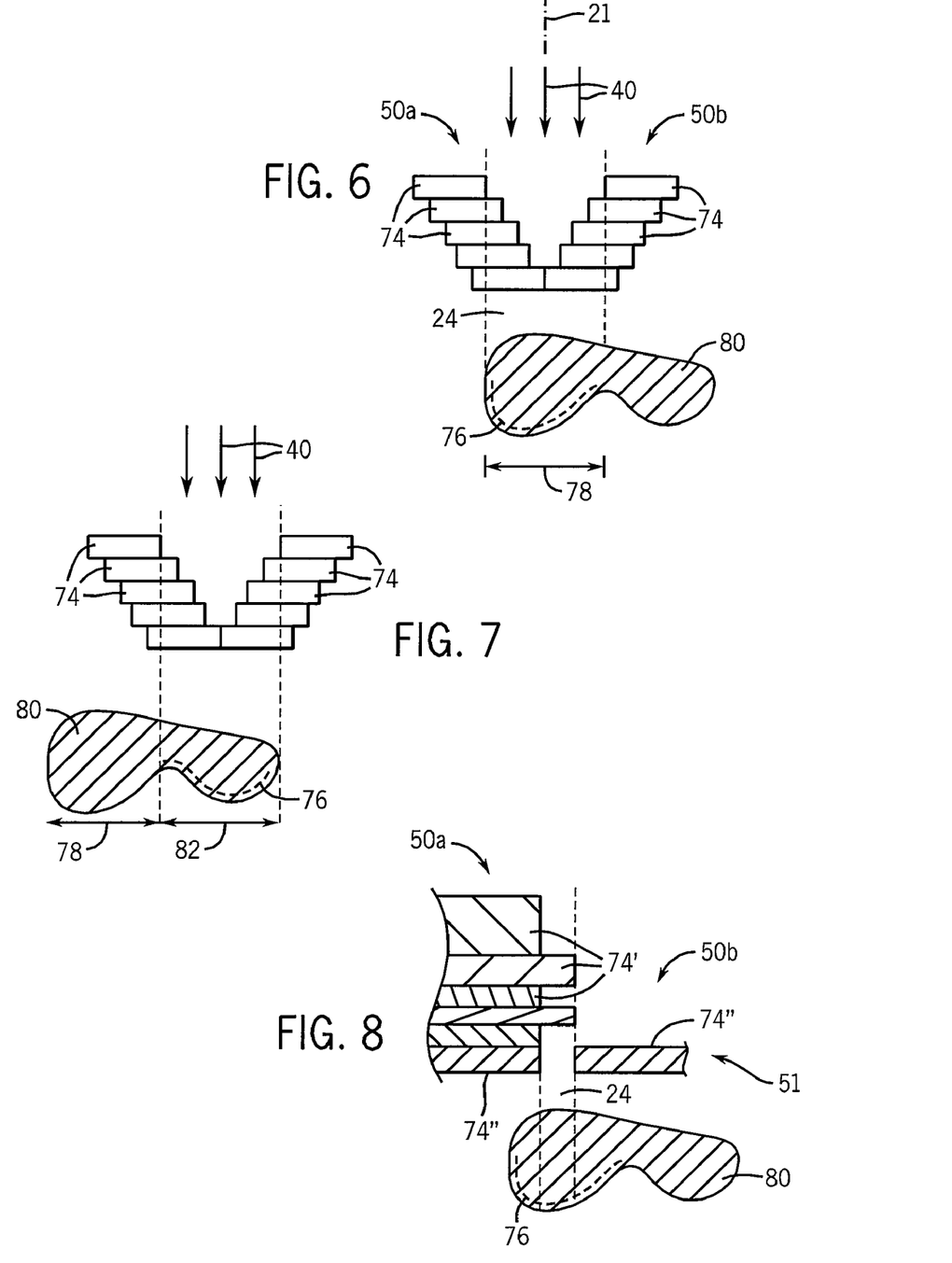
FIG. 6 is a figure similar to that of FIG. 3 showing one shutter of the modulation element of FIG. 5 composed of blades having equal thickness and used to create a piecewise compensator for a tumor.
FIG. 7 is a figure similar to that of FIG. 6 showing a shifting of the blades of the modulator element with respect to FIG. 6 for creation of the piecewise compensator.
FIG. 8 is a figure similar to that of FIG. 6 showing blades with varying thickness used for energy control of a pencil beam.

Referring now to FIG. 6, in one embodiment, the blades 74 of each shutter 50a and 50b may be of equal width along the axis 21, and each blade 74 sized to attenuate the energy in, but not wholly block, the protons of the area beam 40. The blades 74 may be staggered with respect to their overlap along axis 21 to create a thickness through which the area beam 40 must pass that vary longitudinally in the manner of an energy controlling compensator.

When using a distal edge tracking treatment plan, such as that described in U.S. Pat. No. 5,668,371, issued Sep. 16, 1997, assigned to the assignee of the present invention, and hereby incorporated by reference, it may be desired to place the distal edge of the Bragg peaks of the area beam 40 along a convex dose limit 76 within first region 78 of the tumor 80 having a convex distal edge. This convex dose limit 76 is implemented by causing the blades 74 to overlap so that they provide greater total material at the edges of the beamlet 24 than the center of the beamlet 24. The exact amount of curvature may be controlled by controlling the exact amounts of overlap of the blades 74, while only a convex dose limit 76 may be created with these blades and 74. As can be seen by referring to both FIGS. 6 and 7, a tumor 80 with an arbitrarily complex shape may be treated by dividing the tumor 80 into several regions 78 and 82 each of which is independently convex. The blades 74 may then be shifted to provide separate treatment of each region 78 and 82 in a piecewise fashion. The treatment of first region 78 is shown in FIG. 6 and the treatment of second region 82 is shown in FIG. 7.

The particular shape of the convex dose limit 76 is controlled by computer 25 controlling the actuators 56.

Referring now to FIG. 8, alternatively the shutter elements 51 may employ blades 74' having different widths or effective widths (e.g., different attenuation) such that their individual attentions stand, for example, in a base-2 power sequence. In this case, each blade 74 starting at the least attenuating blade 74 may attenuate twice as strongly as the previous blade 74 with which it may overlap. In this way, the minimum number of blades 74 can be used to create the maximum number of energy steps in the beamlet 24. A pair of opposed shutters 50a and 50b each having multiple blades 74 may be used, or, as shown, a single shutter 50a of energy attenuating blades 74 may be used together with two shutters 50a and 50b of ion blocking blades 74" used for intensity modulation.

The use of the binary weighted blades 74 does not allow an intuitive generation of a compensator per the approach of FIGS. 6 and 7 but allows complete control of the energy of the beamlet 24 that may be scanned as described generally in the embodiment of FIG. 2 to create an arbitrary convex dose limit 76 in a tumor 80. In the embodiment shown in FIG. 8, the scanning is conducted by simultaneous movement of a single set of blades 74 within a beamlet 24 defined by ion-opaque blades 74 of shutters 50a and 50b of an area modulator 59 optionally positioned as shown in FIG. 5.

Figure 9:
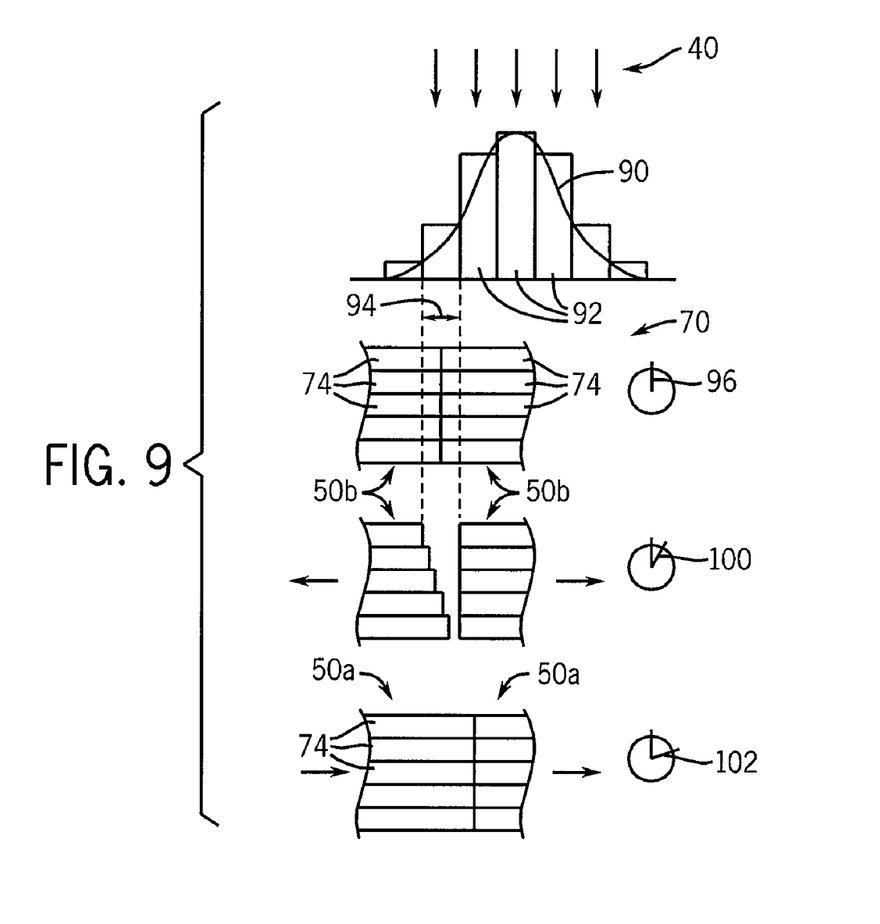
FIG. 9 is a side elevational view of an intensity variation along a longitudinal axis through the area beam and showing use of the blades of FIG. 6 for both intensity and energy control according to the variable intensity of the area beam.

Referring now to FIG. 9, the ability of the present invention to control the intensity of the area beam 40 at different longitudinal and latitudinal positions allows the invention to correct for an irregular intensity profile 90 of the area beam 40 by action of the shutter pairs 51. In one such implementation, the shutter system of FIGS. 6 and 7 may be used to control both intensity and energy by selecting energy attenuating blades 74 that fully block the area beam 40 when all blades 74 overlap.

In this technique, the intensity profile 90 is measured and divided into longitudinal bands 92 where the intensity may be approximated as uniform. The width of the bands 92 is determined by the amount of intensity variation that can be tolerated.

For each band 92, its latitudinal extent is used to define a treatment region 94, the different treatment regions 94 separately treated in sequence. Per this technique, at a first time 96, the blades 74 of each of shutters 50*a* and 50*b* are closed against each other to fully block the area beam 40. The interface between the blades 74 may be aligned with the center of the first treatment region 94.

At a second time 100, the blades 74 are retracted about the center line to create a desired compensator shape assuming a uniform intensity of the area beam within the region 94 equal to its average intensity within the band 92.

At a next time 102, the blades 74 are closed against each other again to fully block the area beam 40. Their interface may then be aligned with a second band 92 and this process repeated. The amount of time between time 96 and 102 controls the intensity of radiation within the treatment region 94, whereas the staggering of the blades 74 during time 100 controls the energy distribution and thus the depth profile of the protons.

Referring again to FIG. 1, the improved treatment speed of the present invention and elimination of the need for multiple custom compensators allows multiple angles of treatment to be obtained by rotating the gantry 12 to different positions within the orbit 16 and applying the radiation as modulated by the present invention at each position. The orbit 16 is a relative orbit with respect to the patient and, of course, may in fact be implemented by rotation of the patient in certain circumstances. In that case the gantry should be understood to be any system for making relative rotations between the patient and the beam.

It is specifically intended that the present invention not be limited to the embodiments and illustrations contained herein and the claims should be understood to include modified forms of those embodiments including portions of the embodiments and combinations of elements of different embodiments as come within the scope of the following claims.

We claim:

1. A method of modulating at least one of the intensity and range of ions comprising:
   (a) generating an area beam of ions directed along an axis and having a longitudinal and latitudinal extent in cross-section;
   (b) controllably occluding an area of beam with a set of longitudinally opposed latitudinally adjacent shutter pairs, each shutter of the pair controllably extended to different longitudinal distances simultaneously to control multiple discrete ion beams at different adjacent latitudinal positions and control independent longitudinal positions such that at least one of an intensity and energy of the ion beams may be independently controlled among ion beams;
   whereby parallel multiple beam treatment over an area may be obtained.

2. The method of claim 1 wherein each shutter pair comprises opposed shutters each sized to fully block the ion beam from passing through the shutter and wherein the shutter pair is controlled to control a dwell time of an aperture formed between the shutters to control the intensity of the ion beam at a variety of longitudinal locations.

3. The method of claim 2 wherein the shutters of the shutter pairs are controlled both to control a center of an aperture created between the shutter pairs and a longitudinal separation between the shutter pairs whereby the longitudinal dimension of the ion beams may be controlled independently from their longitudinal position.

4. The method of claim 1 wherein each shutter comprises multiple blades each sized to only partially attenuate the energy of the ion beam passing through the blade and wherein multiple blades are independently controlled to control an amount of overlap among the blades and a longitudinal location of the overlap to control the energy of the ion beam at a variety of longitudinal locations.

5. The method of claim 4 wherein the multiple blades of each shutter pair when fully overlapping along an axis of the ion beam block passage of the ion beam and wherein the multiple blades of each shutter pair are further controlled to control a dwell time of an aperture formed between the multiple blades to control the intensity of the ion beam at a variety of longitudinal locations.

6. The method of claim 5 wherein the area beam has a non-uniform intensity distribution and the dwell time is controlled according to the non-uniform intensity distribution and a desired treatment intensity to correct for the non-uniform intensity distribution.

7. The method of claim 4 further including the step of:
   (c) controllably occluding an area of the beam with a second set of longitudinally opposed latitudinally adjacent shutter pairs, the shutters of each shutter pair sized to fully block the ion beam from passing through a shutter of the shutter pair, each shutter of the shutter pair controllably extended to different longitudinal distances to control a dwell time of an aperture formed between the shutters to control the intensity of the ion beam at a variety of longitudinal locations.

8. The method of claim 4 wherein the multiple blades when fully overlapping completely block the ion beam from passing through the blades and wherein the blades are controlled in a first state to have selective overlap to control energy and in a second state to fully block the ion beam to control intensity through dwell time adjustment.

9. The method of claim 4 wherein the blades of each shutter pair have equal thickness.

10. The method of claim 4 wherein the blades of each shutter pair have different thicknesses according to a binary sequence.

11. The method of claim 4 wherein the multiple shutters are arranged to provide a treatment surface defined by Bragg peaks of the ion beam at different longitudinal locations and including the step of dividing a treatment area up into multiple, longitudinal surfaces for sequential treatment of each surface.

12. The method of claim 1 wherein the area beam is a proton beam.

13. The method of claim 1 including the step of rotating an axis of the area beam about a patient to provide treatment of the patient at a plurality of angles.

14. An area modulator for an area beam of ions directed along an axis and having a longitudinal and latitudinal extent in cross-section, the modulator comprising:
   a set of longitudinally opposed latitudinally adjacent shutter pairs; and
   an actuator system controllably extending the shutters to different longitudinal distances simultaneously to control multiple discrete ion beams at different, adjacent latitudinal positions and controllable independent longitudinal positions such that at least one of an intensity and energy of the ion beams may be independently controlled among different ion beams;
   whereby parallel multiple beam treatment over an area may be obtained.

15. The modulator of claim 14 wherein each shutter pair comprises opposed shutters each sized to fully block the ion beam from passing through the shutter and wherein the actuator system controls a dwell time of an aperture formed between the shutters to control the intensity of the ion beam at a variety of longitudinal locations.

16. The modulator of claim 15 wherein the actuator system controls the shutters of the shutter pairs to control a center of an aperture created between the shutter pairs and a longitudinal separation between the shutter pairs whereby the longitudinal dimension of the ion beams may be controlled independently from their longitudinal position.

17. The modulator of claim 14 wherein each shutter comprises multiple blades each sized to only partially attenuate the energy of the ion beam passing through the blade and wherein the actuator system independently controls the multiple blades to control an amount of overlap among the blades and a longitudinal location of the overlap to control the energy of the ion beam at a variety of longitudinal locations.

18. The modulator of claim 15 wherein the multiple blades of each shutter pair when fully overlapping along an axis of the ion beam block passage of the ion beam and wherein the actuator system controls the multiple blades of each shutter pair to control a dwell time of an aperture formed between the multiple blades to control the intensity of the ion been at a variety of longitudinal locations.

19. The modulator of claim 17 further including a second set of longitudinally opposed latitudinally adjacent shutter pairs, the shutters of each shutter pair sized to fully block the ion beam from passing through the shutter, wherein the actuator system controls each shutter of the pair to different longitudinal distances to control a dwell time of an aperture formed between the shutters to control the intensity of the ion beam at a variety of longitudinal locations.

20. The modulator of claim 17 wherein the multiple blades when fully overlapping completely block the ion beam from passing through the blades and wherein the actuator system controls the blades in a first state to have selective overlap to control energy and in a second state to fully block the ion beam to control intensity through dwell time adjustment.

21. The modulator of claim 17 wherein the blades of each shutter pair have equal thickness.

22. The modulator of claim 17 wherein the blades of each shutter pair have different thicknesses according to a binary sequence.

23. The modulator of claim 15 wherein the area beam has a non-uniform intensity distribution and the actuator system controls dwell time according to the non-uniform intensity distribution and a desired treatment intensity to correct for the non-uniform intensity distribution.

24. The modulator of claim 17 wherein the multiple shutters are arranged to provide a treatment surface defined by Bragg peaks of the ion beam at different longitudinal locations and the actuator system controls the shutters to provide sequential treatment of multiple, longitudinal surfaces a tumor.

25. The modulator of claim 14 including a gantry for rotating the modulator about a patient to provide treatment of the patient at a plurality of angles.

\* \* \* \* \*

UNITED STATES PATENT AND TRADEMARK OFFICE
CERTIFICATE OF CORRECTION

PATENT NO. : 7,977,648 B2
APPLICATION NO. : 12/305554
DATED : July 12, 2011
INVENTOR(S) : David C. Westerly et al.

It is certified that error appears in the above-identified patent and that said Letters Patent is hereby corrected as shown below:

IN THE SPECIFICATION

Column 6, line 31, please amend as follows:

-- ~~attentions~~ attenuations stand, for example, in a base-2 power sequence. --

Signed and Sealed this
Ninth Day of July, 2013

Teresa Stanek Rea
*Acting Director of the United States Patent and Trademark Office*